(12) United States Patent
Kanaya et al.

(10) Patent No.: US 8,496,968 B2
(45) Date of Patent: Jul. 30, 2013

(54) METHOD FOR PRODUCTION OF MICROCAPSULES USING SOLID FAT (75) Inventors: Kento Kanaya, Hyogo (JP); Masao Sato, Hyogo (JP); Akihisa Kanda, Hyogo (JP)

(73) Assignee: Kaneka Corporation, Osaka (JP)

( * ) Notice: Subject to any disclaimer, the term of this patent is extended or adjusted under 35 U.S.C. 154(b) by 293 days.

(21) Appl. No.: 12/741,565

(22) PCT Filed: Nov. 6, 2008

(86) PCT No.: PCT/JP2008/003206
§ 371 (c)(1),
(2), (4) Date: Aug. 16, 2010

(87) PCT Pub. No.: WO2009/060609
PCT Pub. Date: May 14, 2009

(65) Prior Publication Data
US 2010/0297222 A1    Nov. 25, 2010

(30) Foreign Application Priority Data

Nov. 7, 2007  (JP) ................................ 2007-289826
Sep. 1, 2008  (JP) ................................ 2008-223291

(51) Int. Cl.
*A61K 9/14*    (2006.01)
*A61K 9/16*    (2006.01)

(52) U.S. Cl.
USPC .......................................... 424/490; 424/489

(58) Field of Classification Search
None
See application file for complete search history.

(56) References Cited

U.S. PATENT DOCUMENTS

| 6,113,941 A * | 9/2000 | Takada et al. ................. 424/451 |
| 2001/0018072 A1 * | 8/2001 | Unger ........................... 424/484 |
| 2003/0008040 A1 * | 1/2003 | Soeda et al. .................... 426/98 |
| 2005/0064039 A1 | 3/2005 | Futo et al. |
| 2006/0099244 A1 | 5/2006 | Guilford |
| 2007/0196400 A1 | 8/2007 | Raschke et al. |
| 2007/0207138 A1 | 9/2007 | Goto et al. |
| 2008/0089913 A1 | 4/2008 | Kallmayer et al. |

FOREIGN PATENT DOCUMENTS

| JP | 3102990 B2 | 3/1995 |
| JP | 2003-252751 A | 9/2003 |
| JP | 2004-008015 A | 1/2004 |
| JP | 2004-008837 A | 1/2004 |
| JP | 2007-503418 A | 2/2007 |
| JP | 2007-181421 A | 7/2007 |
| WO | 2005/094789 A1 | 10/2005 |

* cited by examiner

*Primary Examiner* — Susan Tran
(74) *Attorney, Agent, or Firm* — Sughrue Mion, PLLC (57) ABSTRACT A method for production of fine microcapsules which encapsulate a hydrophilic bioactive substance at a high content and can be used in wide range of applications such as foods and medical drugs, which method enabling efficient industrial production, is provided. A method for production of S/O type microcapsules including the steps of: (1) emulsifying and dispersing a mixture of a solid fat and an aqueous solution containing a hydrophilic bioactive substance at a temperature of at least the melting point of the solid fat to obtain a W/O emulsion; (2) removing moisture in the W/O emulsion at a temperature of at least the melting point and lower than the boiling point of the solid fat to obtain an S/O suspension; (3) adding the S/O suspension into an aqueous phase containing at least one selected from a surfactant (B), a thickening agent and a hydrophilic organic solvent, and permitting liquid droplet dispersion at a temperature of at least the melting point and lower than the boiling point of the solid fat to obtain an S/O/W emulsion; and (4) cooling the S/O/W emulsion to lower than the melting point of the solid fat to harden the solid fat, and further removing the moisture at a temperature lower than the melting point of the solid fat.

16 Claims, 1 Drawing Sheet

METHOD FOR PRODUCTION OF MICROCAPSULES USING SOLID FAT

CROSS REFERENCE TO RELATED APPLICATIONS

This application is a National Stage of International Application No. PCT/JP2008/003206 filed Nov. 6, 2008, claiming priority based on Japanese Patent Application Nos. 2007-289826 and 2008-223291, filed Nov. 7, 2007 and Sep. 1, 2008 respectively, the contents of all of which are incorporated herein by reference in their entirety.

TECHNICAL FIELD

The present invention relates to a method for production of microcapsules using a solid fat. More particularly, the present invention relates to a production method for obtaining S/O type microcapsules in which a hydrophilic bioactive substance is polydispersed in a solid fat matrix, and to S/O type microcapsules obtained by the method.

BACKGROUND ART

Conventional methods for producing solid form microcapsules can be generally classified into chemical methods such as an interfacial polymerization method and an in-situ polymerization method; physical/chemical methods such as a coacervation method, an interfacial precipitation method, a liquid phase drying method and a liquid phase film hardening method (orifice method); and mechanical methods such as a spray drying method, a spray cooling method, a dry blending method and a membrane emulsification method. Among these, as methods for producing microcapsules in which a hydrophilic substance is encapsulated, techniques such as an interfacial polymerization method, an in-situ polymerization method, a liquid phase drying method, an liquid phase film hardening method (orifice method), a spray drying method, a spray cooling method, a membrane emulsification method and the like have been known.

Patent Document 1 discloses an example of capsulation of a core substance that is easily affected from an acid, moisture or heat, by a liquid phase film hardening method (orifice method) using a multinozzle. Since the capsules produced by this method will have a mononuclear type capsule structure, it is advantageous in capability of increasing the content of the core substance, and availability of capsules having a seamless structure, and the like. However, the produced capsules often have a large particle size with a diameter in the order of several mm, and the degree of freedom of selectable particle size range is low, leading to a problem of difficulty in application and development to a variety of fields such as use as soft capsules, tablets, and the like.

On the other hand, known microcapsules produced using an emulsion include, for example, microcapsules having an S/O type or W/O type structure.

S/O type or W/O type microcapsules can be applied to a large variety of use such as foods, trophic foods, specified health foods, medical drugs, cosmetics, feeds, pesticides and the like by enclosing a substance that contains a useful component in a liquid or solid form oil phase. In production of microcapsules of such applications, there exist demands for improvement of yield in producing the capsules, increase in the content of the enclosed substance, a wide range of choice of the capsule particle size, and control of release pattern of the core substance and the like in light of DDS.

Furthermore, in the case of W/O type solid form microcapsules, there arise problems of storage stability of the microcapsules such as putrefaction of the moisture encapsulated in the microcapsule, hydrolysis of the bioactive substance dissolved in the moisture, and the like. Additionally, in regard to the method for production, for example, when W/O type solid form microcapsules are obtained after forming a W/O/W emulsion in the liquid phase, the aqueous phase containing a bioactive substance polydispersed in an oil phase likely generates a driving force to the external side of the droplets dispersed in the oil phase due to the surface tension. Thus, this driving force promotes leakage of the bioactive substance to the external aqueous phase, and may lead to decrease in encapsulation yield of the bioactive substance in the microcapsules.

To the contrary, in the case of S/O type microcapsules, since a bioactive substance in a solid form is polydispersed in the microcapsules, the moisture content is comparatively low, and putrefaction or degradation of the bioactive substance less likely occurs. In addition, even though the bioactive substance in a solid form polydispersed in the oil phase forms oil droplets, they would be less subject to a great driving force that results from the surface tension.

However, as a method for production of S/O type microcapsules which has been known heretofore, for example, a liquid phase drying method (Patent Document 2) is exemplified: In this method, organic solvents that are deleterious to the human body such as halogenated hydrocarbons or ethers are used in the production process of the microcapsules; therefore, application to usage for foods is difficult. Moreover, the microcapsules produced by the liquid phase drying method have problems of physical fine pores which are likely to be formed on the capsule film, and leakage of the core substance likely to occur toward outside the membrane, and the like, contrary to an advantage that utilization as sustained release microcapsules is enabled.

Additionally, an example of producing S/O type microcapsules by membrane emulsification utilizing a solid fat as a shell material to prepare a fine W/O/W emulsion, followed by freeze-drying was proposed (Patent Document 3). However, increase in the content of the core substance is difficult, and problems of pressure loss and clogging that may occur during membrane emulsification, as well as durability of the membrane and the like are involved. Therefore it has been difficult to ensure a production amount suited for industrial production.

Meanwhile, glutathione is a tripeptide composed of three amino acids of glutamic acid, glycine and cysteine, and is an antioxidative substance which widely distributes in tissues of living bodies. Glutathione has been found to have an effect of detoxicating detrimental substances that may cause variation or deterioration of cellular functions in a body to strengthen liver functions. Additionally, glutathione serves in suppressing production of lipid peroxide which has been considered to bring about aging and malignant transformation of cells, or protecting a body from lipid peroxide already produced. In these regards, glutathione is reportedly effective in preventing, in general, chronic hepatic diseases such as alcoholic fatty liver, as well as corneal injury, skin disorder, medicinal poisoning, gestosis, leukopenia due to radiation or anticancer agent and the like, and also referred to as having an efficacious action on stress.

So far, attempts for permitting oral ingestion of glutathione have been made by admixing in a food or a supplement; however, achieving sufficient pharmacologic effects is reportedly impossible in many cases due to degradation by digestive enzymes and low absorptivity from the gastrointestinal tract. As an effective administration form of glutathione, intravenous injection has been generally employed.

Moreover, according to Patent Document 4, a liposome preparation enclosing glutathione was investigated in an attempt to improve oral absorptivity; however, liposome is accompanied by a problem of shelf life of the preparation.

Typical imidazole dipeptides include anserine, carnosine and the like which are dipeptides in which α-alanine and L-histidine or a derivative thereof are bonded. Of these, anserine is a substance included in a large quantity in fishes such as skipjack, tuna, salmon and shark as well as in the muscle of chicken. The imidazole dipeptides such as anserine have a high buffer capacity in a physiological pH range and have been verified to be effective in maintaining physical capabilities and resisting against fatigue by suppressing lowering of muscular pH due to lactate accumulation and the like, and reportedly have functions such as an uric acid level suppressing action, an active oxygen scavenging action, an blood pressure lowering action and an anti-inflammatory action.

With respect to formulation of the imidazole dipeptides, they are generally prepared by tableting or filling in a hard capsule. However, since degradation by digestive enzymes can occur in oral ingestion, carrying out a treatment such as protection of the preparation from gastric acid and the like is believed to be necessary in order to achieve the pharmacologic effects efficiently.

Additionally, although bulk powders of anserine are purified from fishes, in general, by steps of extraction, desalting, drying and the like. Thus resulting anserine bulk powders are known to have a low bulk density, and inferior powder flow characteristics. They are often mixed usually with an excipient such as dextrin to obtain the preparation. Accordingly, preparation of bulk powders containing anserine at a high content has been recognized as being difficult. Moreover, the anserine bulk powders derived from fishes often have remaining unpleasant odor constituents peculiar to fishes, which may raise problems such as restraints in oral ingestion, and the like.

Patent Document 1: JP No. 3,102,990
Patent Document 2: JP-A No. 2003-252751
Patent Document 3: JP-A No. 2004-8015
Patent Document 4: United States Patent Application, Publication No. 2006/0099244

DISCLOSURE OF THE INVENTION

Problems to be Solved by the Invention

Conventional methods for producing microcapsules that enclose hydrophilic components are accompanied by problems in terms of production and safety to meet food standards, such as difficulty in controlling the capsule diameter, insufficient contents of the core substance and yields in production, as well as possible necessity for using organic solvents which have been restricted for applications in foods, and the like.

An object of the present invention is to provide a method for production of fine microcapsules which encapsulate a hydrophilic bioactive substance at a high content and can be used in wide range of applications such as foods and medical drugs, which method enabling efficient industrial production.

Means for Solving the Problems

As a result of investigation conducted elaborately in order to solve the foregoing problems, a method for production of fine microcapsules which encapsulate a hydrophilic bioactive substance at a high content and can be used in wide range of applications such as foods and medical drugs, which method enabling efficient industrial production, was found by carrying out four steps of: (1) emulsifying and dispersing a mixture of the solid fat and an aqueous solution containing the hydrophilic bioactive substance at a temperature of at least the melting point of the solid fat to obtain a W/O emulsion; (2) removing moisture in the W/O emulsion at a temperature of at least the melting point and lower than the boiling point of the solid fat to obtain an S/O suspension; (3) adding the S/O suspension into an aqueous phase and permitting liquid droplet dispersion at a temperature of at least the melting point and lower than the boiling point of the solid fat to obtain an S/O/W emulsion; and (4) cooling the S/O/W emulsion to lower than the melting point of the solid fat to harden the solid fat, and further removing the moisture at a temperature lower than the melting point of the solid fat. Accordingly, the present invention was accomplished.

More specifically, a first aspect of the present invention provides a method for production of S/O type microcapsules in which a hydrophilic bioactive substance is polydispersed in a solid fat matrix characterized by including four steps of: (1) emulsifying and dispersing a mixture of the solid fat and an aqueous solution containing the hydrophilic bioactive substance at a temperature of at least the melting point of the solid fat to obtain a W/O emulsion; (2) removing moisture in the W/O emulsion at a temperature of at least the melting point and lower than the boiling point of the solid fat to obtain an S/O suspension; (3) adding the S/O suspension into an aqueous phase containing at least one selected from a surfactant (B), a thickening agent and a hydrophilic organic solvent, and permitting liquid droplet dispersion at a temperature of at least the melting point and lower than the boiling point of the solid fat to obtain an S/O/W emulsion; and (4) cooling the S/O/W emulsion to lower than the melting point of the solid fat to harden the solid fat, and further removing the moisture at a temperature lower than the melting point of the solid fat. In addition, the present invention also relates to S/O type microcapsules characterized by polydispersion of glutathione or an imidazole dipeptide in a solid fat matrix.

Effects of the Invention

According to the method for production of S/O type microcapsules of the present invention, efficient industrial production of S/O type microcapsules is enabled, while capable of increasing the content of a hydrophilic bioactive substance in the capsule, and of controlling a wide range of capsule particle size, which could be hardly achieved according to conventional methods for producing S/O type microcapsules. Moreover, the method for production of the present invention also enables S/O type microcapsules stably retaining a substance enclosed therein to be produced without using an organic solvent etc., which is detrimental to the human body in the production steps, and thus it enables realizing application and development to a wide range not only fields of medical drugs, pesticides and the like, but also fields of foods with ease.

Moreover, the present invention enables production of enteric S/O type microcapsules by using as a matrix of the microcapsules a fat and oil component which is degradable by lipase. More specifically, the S/O type microcapsules of the present invention can be produced in the form of a preparation which enables a hydrophilic bioactive substance that is easily degradable in stomach such as glutathione to be absorbed efficiently in intestine without being degraded in stomach.

BEST MODE FOR CARRYING OUT THE INVENTION

Hereinafter, embodiments of the present invention are described in detail.

The present invention provides a method for production of S/O type microcapsules in which a hydrophilic bioactive substance is polydispersed in a solid fat matrix, the method including the following steps (1) to (4):

(1) emulsifying and dispersing a mixture of the solid fat and an aqueous solution containing the hydrophilic bioactive substance at a temperature of at least the melting point of the solid fat to obtain a W/O emulsion;

(2) removing moisture in the W/O emulsion at a temperature of at least the melting point and lower than the boiling point of the solid fat to obtain an S/O suspension;

(3) adding the S/O suspension into an aqueous phase containing at least one selected from a surfactant (B), a thickening agent and a hydrophilic organic solvent, and permitting liquid droplet dispersion at a temperature of at least the melting point and lower than the boiling point of the solid fat to obtain an S/O/W emulsion; and (4) cooling the S/O/W emulsion to lower than the melting point of the solid fat to harden the solid fat, and further removing the moisture at a temperature lower than the melting point of the solid fat.

The S/O type microcapsule in the method for production of the present invention means a solid particle in which a hydrophilic solid substance is polydispersed in a solid oil phase, and is distinct from an S/O suspension in which a solid substance is dispersed in a liquid oil phase, or an S/O/W emulsion in which an S/O suspension is suspended in an aqueous phase.

The hydrophilic bioactive substance to be encapsulated in the S/O type microcapsules in the method for production of the present invention may be selected ad libitum depending on the application as long as it is water soluble and is solid at ordinary temperatures. It is to be noted that the ordinary temperature referred to herein means a temperature of 20° C. Examples of the hydrophilic bioactive substance include proteins, peptides, amino acids, antibiotics, nucleic acids, organic acids, water soluble vitamins, water soluble coenzymes, minerals, saccharide, lecithins, and the like.

The proteins may include, for example, enzymes, antibodies, antigens, hormones and the like, and specific examples include proteases, amylases, cellulases, kinases, glucanases, pectinases, isomerases, lipases, pectinases, interferon, interleukin, BMP, immunoglobulin and the like.

Examples of the peptides include luteinizing hormone releasing hormone (LH-RH), insulin, somatostatin, growth hormone, growth hormone releasing hormone (GH-RH), prolactin, erythropoietin, adrenocortical hormone, melanocyte stimulating hormone, thyrotropin releasing hormone (TRH), thyroid stimulating hormone, luteinizing hormone, follicle stimulating hormone, vasopressin, oxytocin, calcitonin, gastrin, secretin, pancreozymin, cholecystokinin, angiotensin, human placental lactogen, human chorionic gonadotropin, enkephalin, endorphin, kyotorphin, tuftsin, thymopoietin, thymosin, thymothymulin, thymic humoral factors, blood thymic factors, tumor necrosis factors, colony inducing factors, motilin, dynorphin, bombesin, neurotensin, cerulein, bradykinin, glutathione, imidazole dipeptides (carnosine, anserine, homoanserine, balenine, aspartame and the like), atrial natriuretic factors, nerve growth factors, cell growth factors, neurotrophic factors, peptides having endothelin antagonism etc., and derivatives thereof, as well as fragments thereof or derivatives of such fragments, and the like.

Specific examples of the amino acids include glycine, alanine, valine, leucine, isoleucine, phenylalanine, tyrosine, tryptophan, serine, threonine, proline, hydroxyproline, cysteine, methionine, aspartic acid, glutamic acid, lysine, arginine, histidine, and the like.

The antibiotics may include, for example, β-lactam type, aminoglycoside type, tetracyclin type, chloramphenicol type, macrolide type, ketolide type, polyene macrolide type, glycopeptide type, nucleic acid type, pyridonecarboxylic acid type antibiotics and the like.

Specific examples of the nucleic acids include inosinic acid, guanylic acid, xanthylic acid, ATP, GTP, DNA, RNA, and the like.

Specific examples of the organic acids include citric acid, succinic acid, fumaric acid, lactic acid, gluconic acid, malic acid, tartaric acid, pyruvic acid, and the like.

Specific examples of the water soluble vitamins include vitamin $B_1$, vitamin $B_2$, vitamin $B_6$, vitamin $B_{12}$, ascorbic acid, niacin, pantothenic acid, folic acid, lipoic acid, biotin, and the like.

The water soluble coenzymes may include thiamine diphosphate, NADH, NAD, NADP, NADPH, FMN, FAD, coenzyme A, pyridoxal phosphate, tetrahydrofolic acid, and the like.

The minerals may include, for example, calcium, magnesium, iron, zinc, potassium, sodium, copper, vanadium, manganese, selenium, molybdenum, cobalt and the like, as well as compounds to which such a mineral is bonded, and the like.

The saccharides may include, for example, monosaccharides, disaccharides, oligosaccharides, sugar alcohols, other polysaccharides, and the like. Specific examples of the monosaccharide include arabinose, xylose, ribose, glucose, fructose, galactose, mannose, sorbose, rhamnose, and the like. Specific examples of the disaccharide include maltose, cellobiose, trehalose, lactose, sucrose, and the like. Specific examples of the oligosaccharide include maltotriose, raffinose saccharide, stachyose, and the like. Specific examples of the sugar alcohol include arabitol, xylitol, adonitol, mannitol, sorbitol, dulcitol, and the like. Other polysaccharides may include chitin, chitosan, agarose, heparin, hyaluronic acid, xyloglucan, starch, glycogen, pectin, chondroitin sulfate, heparan sulfate, keratan sulfate, and the like.

The lecithins may include, for example, egg yolk lecithin, soybean lecithin, phosphatidylcholine, phosphatidylethanolamine, phosphatidylserine, sphingomyelin, dicetylphosphoric acid, stearylamine, phosphatidylglycerol, phosphatidic acid, phosphatidylinositolamine, cardiolipin, ceramidephosphorylethanolamine, ceramidephosphorylglycerol, lysolecithin, and the like.

The hydrophilic bioactive substances as illustrated hereinabove may be used also in the form of their derivatives or salts as long as they are hydrophilic, and these substances may be used in combination of two or more thereof, as a matter of course.

In the method for production of the present invention, the solid fat used for constructing the matrix of the S/O type microcapsules is not particularly limited as long as it is an oily component or oil-based composition that has a solid form at ordinary temperatures, but preferably has a melting point of at least 40° C., and has a solid form to be less likely to be disintegrated and is of a hard form at ordinary temperatures. The terms "solid", "solid form", "melting point" as herein referred to, when a plurality of components are combined as the solid fat to be used, mean properties as a whole of the mixed composition. Such solid fats (or their constituents) may include, for example, fats and oils, waxes, fatty acids, and the like.

The fats and oils may include, for example, vegetable fats and oils such as e.g., coconut oil, palm oil, palm kernel oil, linseed oil, camellia oil, brown rice germ oil, rapeseed oil, rice oil, peanut oil, olive oil, corn oil, wheat germ oil, soybean oil, perilla oil, cotton seed oil, sunflower seed oil, kapok oil, evening primrose oil, shea butter, sal butter, cacao butter, mango butter, illipe butter, sesame oil, safflower oil and olive oil etc., and animal fats and oils such as e.g., fish oil, beef tallow, milk fat and lard etc. In addition, fats and oils prepared by subjecting the same to processing such as fractionation, hydrogenation, ester exchange or the like. Needless to mention, middle chain fatty acid triglycerides, long chain fatty acid triglycerides, partial glycerides of fatty acids and the like can be also used. Among these fats and oils, saturated long chain fatty acid triglyceride such as tristearin and tripalmitin, as well as natural solid fats such as cacao butter and shea butter, and fractionated fats and oils prepared by fractionation of a high-melting point fraction of hardened natural fats and oils obtained by hydrogenating liquid fats and oils are preferably used in light of favorable availability, and ease in executing melting and hardening by cooling.

The waxes may include, for example, edible waxes such as yellow bees wax, Japanese wax, candelilla wax, rice bran wax, carnuba wax, snow wax, shellac wax, jojoba wax, and the like.

The fatty acids may include, for example, caprylic acid, capric acid, lauric acid, myristic acid, palmitic acid, oleic acid, behenic acid, and esters thereof.

Alternatively, a mixture of the components described above may be used as the solid fat of the present invention, and in this case, any mixture which is solid as a whole at ordinary temperatures is acceptable even though a component that is a liquid at ordinary temperatures is contained.

Further, in the method for production of the present invention, by using a lipid soluble bioactive substance mixed in the solid fat employed, microcapsules containing both a hydrophilic bioactive substance and a lipid soluble bioactive substance can be also obtained. Such a lipid soluble bioactive substance may include, for example, coenzyme $Q_{10}$, lipid soluble vitamins, carotenoid, lipid soluble polyphenol, flavonoid, plant sterols, α-lipoic acid, L-carnitine, and the like.

Although there exist oxidized type and reduced type coenzyme $Q_{10}$, microcapsules can be obtained according to the present invention in either case in which oxidized type coenzyme $Q_{10}$ or reduced type coenzyme $Q_{10}$ is used as the coenzyme $Q_{10}$. Of course, a mixture of oxidized type coenzyme $Q_{10}$ and reduced type coenzyme $Q_{10}$ may be used as the coenzyme $Q_{10}$.

The lipid soluble vitamins may include, for example, vitamin A group such as vitamin A acetate, vitamin A palmitate, vitamin A (retinol), vitamin A aldehyde (retinal) and vitamin A acid, vitamin D group such as cholecalciferol (vitamin D3), ergocalciferol (vitamin D2), 1α, 25-dihydroxycholecalciferol (activity type vitamin D3) and derivatives thereof, vitamin E group such as α-tocopherol and 5,7,8-trimethyl tocotrienol, vitamin K group such as 2-farnesyl-3-methyl-1,4-naphthoquinone (vitamin K2) and 2-methyl-1,4-naphthoquinone (vitamin K3), and the like.

The carotenoid may include, for example, β-carotene, α-carotene, rutin, zeaxanthin, capsanthin, lycopene, β-cryptoxanthin, astaxanthin, canthaxanthin, and the like.

The plant sterols refer to plant sterol or plant stanol obtained from a lipid soluble fraction of a plant and having a structure similar to cholesterol or cholestanol of a saturated type, or constituents of the same. As the plant sterol, for example, β-sitopterol, β-sitostanol, stigmasterol, stigmastanol, campesterol, campestanol, brassicasterol, brassicastanol, ergosterol and the like may be included. As the plant stanol, in addition to natural products, plant sterol saturated by hydrogenation may be also used.

The lipid soluble bioactive substance as illustrated herein may be used in the form of a derivative or a salt thereof as long as it is lipid soluble. The lipid soluble bioactive substance may be used either alone, or two or more may be used in combination.

In the method for production of the present invention, a mixture of the solid fat and an aqueous solution containing the hydrophilic bioactive substance is emulsified and dispersed at a temperature of at least the melting point of the solid fat to obtain a W/O emulsion in the step (1). Herein, the W/O emulsion refers to a water in oil type emulsion in which an aqueous solution of a hydrophilic bioactive substance forming liquid droplets is emulsified and dispersed in a liquid oil phase formed with a melted solid fat. Specifically, the solid fat is first heated to a temperature of at least the melting point to permit melting. In addition, the hydrophilic bioactive substance is separately dissolved in water to prepare an aqueous solution containing a hydrophilic bioactive substance. The melted liquid oil phase component is mixed with the aqueous solution containing a hydrophilic bioactive substance at a temperature of at least the melting point of the solid fat to emulsify and disperse the aqueous solution in the liquid oil phase.

In the method for production of the present invention, the weight ratio of the hydrophilic bioactive substance to the solid fat in the step (1) falls within the range of preferably 0.01/99.99 to 70/30, and more preferably 1/90 to 40/60. When the weight ratio of the hydrophilic bioactive substance relative to the solid fat is low, the content of the hydrophilic bioactive substance in the resulting S/O type microcapsules becomes so low that when, for example, a certain amount of the hydrophilic bioactive substance is orally administered, intake of a large quantity of the microcapsules would be necessary. On the other hand, when the weight ratio of the hydrophilic bioactive substance relative to the solid fat is too high, the encapsulation yield of the hydrophilic bioactive substance is lowered due to leakage of the hydrophilic bioactive substance to the external aqueous phase in the production step, and the like.

In the method for production of the present invention, the feeding proportion of the aqueous phase relative to the oil phase in preparing the W/O emulsion in the step (1), i.e., the feeding proportion of the aqueous solution containing a hydrophilic bioactive substance relative to the melted solid fat, is not particularly limited, but in light of production of the microcapsules encapsulating the core substance at a high content, the feeding proportion of the aqueous phase relative to the oil phase is preferably as high as possible, and the volume ratio of the aqueous phase to the oil phase is preferably 1/99 or above, and particularly preferably 10/90 or above. On the other hand, when the volume ratio of the aqueous phase to the oil phase exceeds 70/30, the aqueous phase droplets dispersed in the oil phase is enlarged excessively, and phenomenon of phase inversion of the oil phase and the aqueous phase may be caused, leading to difficult in preparing a stable W/O emulsion. Accordingly, the volume ratio is preferably 70/30 or below.

Furthermore, the feeding concentration of the hydrophilic bioactive substance in the aqueous phase in the step (1) is not particularly limited, and can be regulated ad libitum depending on the core substance content in the intended microcapsules. However, in terms of improvement of the production efficiency of the microcapsules, the feeding concentration of the hydrophilic bioactive substance in the aqueous phase is preferably as high as possible, and the substance can be fed in the range not exceeding the saturating concentration of the hydrophilic bioactive substance with respect to the aqueous phase.

In the method for production of the present invention, when the W/O emulsion in which the aqueous phase is emulsified and dispersed in the liquid oil phase is prepared in the step (1), the emulsification and dispersion is preferably carried out in the presence of a surfactant (A), and the surfactant (A) is more preferably contained in the oil phase. Moreover, in light of formation of a water droplet dispersion in the oil phase, the HLB of the surfactant (A) is preferably 10 or below, more preferably 7 or below, and most preferably 5 or below. As the surfactant (A), those which can be used for foods or medical drugs are preferred, and examples thereof may include e.g., glycerol esters of fatty acids, sucrose esters of fatty acids, sorbitan esters of fatty acids, and lecithins.

The glycerol esters of fatty acids may include, for example, partial glycerides of fatty acids, polyglycerol esters of fatty acids, polyglycerol condensed ricinoleic acid esters, and the like. The partial glycerides of fatty acids may include, for example, monoglycerol esters of fatty acids such as monoglycerol monocaprylate, monoglycerol monocaprate, monoglycerol dicaprylate, monoglycerol dicaprate, monoglycerol dilaurate, monoglycerol dimyristate, monoglycerol distearate, monoglycerol dioleate, monoglycerol dierucate and monoglycerol dibehenate, monoglycerol esters of fatty acid-organic acids such as monoglycerol caprylate succinate, monoglycerol stearate citrate, monoglycerol stearate acetate, monoglycerol stearate succinate, monoglycerol stearate lactate, monoglycerol stearate diacetyl tartarate and monoglycerol oleate citrate, and the like. The polyglycerol esters of fatty acids may include, for example, esterified products of polyglycerol containing polyglycerol having a degree of polymerization of 2 to 10 as a principal component with fatty acids each having 6 to 22 carbon atoms at one or more hydroxy groups of the polyglycerol. Specific examples include hexaglycerol monocaprylate, hexaglycerol dicaprylate, decaglycerol monocaprylate, triglycerol monolaurate, tetraglycerol monolaurate, pentaglycerol monolaurate, hexaglycerol monolaurate, decaglycerol monolaurate, triglycerol monomyristate, pentaglycerol monomyristate, pentaglycerol trimyristate, hexaglycerol monomyristate, decaglycerol monomyristate, diglycerol monooleate, triglycerol monooleate, tetraglycerol monooleate, pentaglycerol monooleate, hexaglycerol monooleate, decaglycerol monooleate, diglycerol monostearate, triglycerol monostearate, tetraglycerol monostearate, pentaglycerol monostearate, pentaglycerol tristearate, hexaglycerol monostearate, hexaglycerol tristearate, hexaglycerol distearate, decaglycerol monostearate, decaglycerol distearate, decaglycerol tristearate, and the like. In the polyglycerol condensed ricinoleic acid esters, for example, the average degree of polymerization of polyglycerol may be 2 to 10, whereas the average degree of condensation of polyricinoleic acid (average of the number of condensation of ricinoleic acid) may be 2 to 4; and for example, tetraglycerol condensed ricinoleate, pentaglycerol condensed ricinoleate, hexaglycerol condensed ricinoleate, and the like may be included.

The sucrose esters of fatty acids may be include esterified products of sucrose with fatty acids each having carbon atoms of 6 to 22 at one or more hydroxy groups of the sucrose. Specific examples include sucrose palmitate, sucrose stearate, sucrose laurate, sucrose behenate, sucrose erucate, and the like.

The sorbitan esters of fatty acids may be include esterified products of sorbitans with fatty acids each having carbon atoms of 6 to 18, and preferably 6 to 12 at one or more hydroxy groups of the sorbitan. Specific examples include sorbitan monostearate, sorbitan monooleate, and the like.

The lecithins may include, for example, egg yolk lecithin, soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramidephosphorylethanolamine, ceramidephosphorylglycerol, lysolecithin, and mixtures thereof, and the like.

Needless to say, the surfactant (A) herein may be used as a combination of two or more thereof.

In the aforementioned step (1), the concentration of the surfactant (A) in the oil phase is not particularly limited, but the concentration falls within the range of preferably 0.01 to 20% by weight, and more preferably 0.1 to 10% by weight.

When the W/O emulsion is prepared in the step (1) of the method for production of the present invention, it is necessary that the temperature in carrying out the preparation results in melting of the solid fat, i.e., the temperature of at least the melting point of the solid fat. On the other hand, since it is necessary that the emulsification and dispersion is carried out under an operation condition of lower than the boiling point of the solid fat and lower than the boiling point of water in the step (1), the operation is carried out at a temperature the upper limit of which being 100° C. and preferably 90° C. or below at an ordinary pressure. However, when the melting point of the solid fat is at least 100° C., the W/O emulsion can be also prepared under conditions of the temperature being at least 100° C., by adjusting the water vapor pressure so as to avoid evaporation of the moisture by pressurization inside the apparatus.

Furthermore, upon the emulsification and dispersion carried out for preparing the W/O emulsion, a variety of generally used emulsification disperser, for example, a homomixer, homodisperser, homogenizer, high pressure homogenizer, colloid mil, ultrasonic emulsifier, membrane emulsifier or the like can be used.

In the method for production of the present invention, the moisture in the W/O emulsion obtained in the step (1) is removed at a temperature of at least the melting point and lower than the boiling point of the solid fat to prepare an S/O suspension in the following step (2). The S/O suspension refers to a suspension liquid in which a hydrophilic bioactive substance in a solid form is dispersed in a liquid oil phase formed with a melted solid fat. During drying in the step (2), it is preferred to remove the moisture while the dispersion state of the W/O emulsion is maintained, and drying while shearing with an emulsification disperser, a stirrer or the like is preferred. With respect to the temperature conditions in the step (2), it is necessary to adjust the temperature to be at least the melting point of the solid fat and lower than the boiling point of the solid fat, and further at least the boiling point of water. Although the boiling point of water is 100° C. at an ordinary pressure, the temperature, and the pressure conditions are not particularly limited as long as the moisture is evaporated to permit drying, and the operation may be also carried out while reducing the pressure in the apparatus.

As a result of the preparation of the S/O suspension by removing the moisture from the W/O emulsion in the step (2), outflow of the hydrophilic bioactive substance to the external aqueous phase of the S/O/W emulsion becomes less likely to occur in the following step (3) and step (4); therefore, improvement of encapsulation efficiency of the hydrophilic bioactive substance in the microcapsules is enabled. On the other hand, according to conventional methods in which a W/O/W emulsion is prepared from a W/O emulsion, sufficiently high encapsulation efficiency cannot be attained since outflow of the component in the internal aqueous phase to the external aqueous phase is likely to occur in W/O/W emulsions.

Additionally, in order to increase the content of the hydrophilic bioactive substance encapsulated in the S/O type microcapsules obtained through the steps described later, the aqueous solution containing the hydrophilic bioactive substance is further added again to the S/O suspension obtained once in the step (2), followed by emulsification and dispersion to prepare a W/O emulsion again, from which moisture is removed to execute drying, in other words, the steps (1) and (2) are repeated. Accordingly, also preparation of an S/O suspension in which the hydrophilic bioactive substance is polydispersed at a higher concentration is enabled. By repeating such a series of operations several times, to obtain an S/O suspension containing a hydrophilic bioactive substance to a desired concentration is enabled.

In the method for production of the present invention, the S/O suspension of the hydrophilic bioactive substance prepared by the aforementioned method in the step (2) is added to the aqueous phase (external aqueous phase) in the following step (3), and liquid droplet dispersion is permitted at a temperature of at least the melting point and lower than the boiling point of the solid fat to prepare an S/O/W emulsion. Herein, the S/O/W emulsion refers to a suspension liquid in which the S/O suspension of the hydrophilic bioactive substance in the form of liquid droplets is dispersed in the aqueous phase. It is necessary to adjust the temperature condition in the step (3) to a temperature of at least the melting point of the solid fat and lower than the boiling point of the solid fat, and also lower than the boiling point of water such that the oil droplet dispersion in the aqueous phase is enabled. The aqueous phase used in this procedure may be, in light of formation of the oil droplet dispersion in the aqueous phase, has contained beforehand at least one of a surfactant (B), a thickening agent, a hydrophilic organic solvent.

When a surfactant (B) is used in the step (3) of the method for production of the present invention, the HLB of the surfactant (B) is preferably 5 or above, more preferably 7 or above, and most preferably 10 or above in light of formation of the oil droplet dispersion in the aqueous phase. Moreover, the surfactant (B) is preferably one which can be used for foods or medical drugs, and examples thereof include glycerol esters of fatty acids, sucrose esters of fatty acids, sorbitan esters of fatty acids, and lecithins, and the like.

The glycerol esters of fatty acids may include, for example, partial glycerides of fatty acids, polyglycerol esters of fatty acids, polyglycerol condensed ricinoleic acid esters, and the like. The partial glycerides of fatty acids may include, for example, monoglycerol esters of fatty acids such as monoglycerol monocaprylate, monoglycerol monocaprate, monoglycerol dicaprylate, monoglycerol dicaprate, monoglycerol dilaurate, monoglycerol dimyristate, monoglycerol distearate, monoglycerol dioleate, monoglycerol dierucate and monoglycerol dibehenate, monoglycerol esters of fatty acid-organic acids such as monoglycerol caprylate succinate, monoglycerol stearate citrate, monoglycerol stearate acetate, monoglycerol stearate succinate, monoglycerol stearate lactate, monoglycerol stearate diacetyl tartarate and monoglycerol oleate citrate, and the like. The polyglycerol esters of fatty acids may include, for example, esterified products of polyglycerol containing polyglycerol having a degree of polymerization of 2 to 10 as a principal component with fatty acids each having 6 to 22 carbon atoms at one or more hydroxy groups of the polyglycerol. Specific examples include hexaglycerol monocaprylate, hexaglycerol dicaprylate, decaglycerol monocaprylate, triglycerol monolaurate, tetraglycerol monolaurate, pentaglycerol monolaurate, hexaglycerol monolaurate, decaglycerol monolaurate, triglycerol monomyristate, pentaglycerol monomyristate, pentaglycerol trimyristate, hexaglycerol monomyristate, decaglycerol monomyristate, diglycerol monooleate, triglycerol monooleate, tetraglycerol monooleate, pentaglycerol monooleate, hexaglycerol monooleate, decaglycerol monooleate, diglycerol monostearate, triglycerol monostearate, tetraglycerol monostearate, pentaglycerol monostearate, pentaglycerol tristearate, hexaglycerol monostearate, hexaglycerol tristearate, hexaglycerol distearate, decaglycerol monostearate, decaglycerol distearate, decaglycerol tristearate, and the like. In the polyglycerol condensed ricinoleic acid esters, for example, the average degree of polymerization of polyglycerol may be 2 to 10, whereas the average degree of condensation of polyricinoleic acid (average of the number of condensation of ricinoleic acid) may be 2 to 4, and for example, tetraglycerol condensed ricinoleate, pentaglycerol condensed ricinoleate, hexaglycerol condensed ricinoleate, and the like may be included.

The sucrose esters of fatty acids may be include esterified products of sucrose with fatty acids each having carbon atoms of 6 to 18, preferably 6 to 12 at one or more hydroxy groups of sucrose. Specific examples include sucrose palmitate, sucrose stearate, and the like.

The sorbitan esters of fatty acids may be include esterified products of sorbitans with fatty acids each having carbon atoms of 6 to 18, and preferably 6 to 12 at one or more hydroxy groups of sorbitan. Specific examples include sorbitan monostearate, sorbitan monooleate, and the like.

The lecithins may include, for example, egg yolk lecithin, soybean lecithin, phosphatidylcholine, phosphatidylethanolamine, phosphatidylserine, sphingomyelin, dicetyl phosphate, stearylamine, phosphatidylglycerol, phosphatidic acid, phosphatidylinositolamine, cardiolipin, ceramidephosphorylethanolamine, ceramidephosphorylglycerol, lysolecithin, and mixtures thereof, and the like.

Needless to say, the surfactant (B) herein may be used as a combination of two or more thereof.

When the surfactant (B) is used in the aforementioned step (3), the concentration of the surfactant (B) contained in the aqueous phase is not particularly limited, but the concentration falls within the range of preferably 0.001 to 5% by weight, and more preferably, 0.01 to 1% by weight.

Although the thickening agent when used in the step (3) of the method for production of the present invention is not particularly limited, those which can be used for foods or medical drugs are preferred. Such a thickening agent may include, for example, gum arabic, gelatin, agar, starch, carrageenan, casein, alginic acids, saccharide, pullulan, celluloses, xanthan gum, guar gum, tamarind seed gum, and polyvinyl alcohol, and the like.

The alginic acids may include, for example, alginic acid, sodium alginate, potassium alginate, and the like.

The saccharides may include, for example, monosaccharides, disaccharides, oligosaccharides, sugar alcohols, other polysaccharides, and the like. Specific examples of the monosaccharide include arabinose, xylose, ribose, glucose, fructose, galactose, mannose, sorbose, rhamnose, and the like. Specific examples of the disaccharide include maltose, cellobiose, trehalose, lactose, sucrose, and the like. Specific examples of the oligosaccharide include maltotriose, raffinose saccharide, stachyose, and. the like. Specific examples of the sugar alcohol include arabitol, xylitol, adonitol, mannitol, sorbitol, dulcitol, and the like. Other polysaccharides may include chitin, chitosan, agarose, heparin, hyaluronic acid, xyloglucan, starch, glycogen, pectin, chondroitin sulfate, heparan sulfate, keratan sulfate, and the like.

The celluloses may include, for example, crystalline cellulose, hydroxymethylcellulose, hydroxyethylcellulose, hydroxyethylmethylcellulose, carboxymethylcellulose, methylcelluloseand the like.

The thickening agent as illustrated herein may be used in combination of two or more thereof.

When the thickening agent is used in the step (3), the concentration of the thickening agent contained in the aqueous phase is not particularly limited, but the concentration falls within the range of preferably 0.001 to 10% by weight, and more preferably, 0.005 to 3% by weight, with respect to water.

In the step (3) of the method for production of the present invention, for preparing a homogeneous and highly stable S/O/W emulsion, the liquid droplet dispersion may be also carried out in the presence of an aqueous phase containing a hydrophilic organic solvent. The hydrophilic organic solvent is not particularly limited as long as it is readily dissolvable in the aqueous phase, and enables the S/O suspension to be dispersed in the form of oil droplets at a temperature of at least the melting point of the oil phase in the aqueous phase dissolved therein, and for example, ketones, alcohols, nitriles, ethers and the like may be included.

The ketones are not particularly limited, and may include acetone, methyl ethyl ketone, and the like.

The alcohols are not particularly limited, which may be either cyclic or noncyclic, and may be either saturated or unsaturated, but in general, saturated alcohols are preferably used. Among all, monohydric alcohols having 1 to 5 carbon atoms, dihydric alcohols having 2 to 5 carbon atoms, and trihydric alcohols having 3 carbon atoms are preferred. Specific examples of the monohydric alcohol include methanol, ethanol, 1-propanol, 2-propanol, 1-butanol, 2-butanol, isobutyl alcohol, 1-pentanol, 2-pentanol, 3-pentanol, and the like. Specific examples of the dihydric alcohol include 1,2-ethanediol, 1,2-propanediol, 1,3-propanediol, 1,2-butanediol, 1,3-butanediol, 1,4-butanediol, 2,3-butanediol, 1,5-pentanediol, and the like. Specific examples of the trihydric alcohol include glycerol, and the like.

The nitriles are not particularly limited, which may be either cyclic or noncyclic, and may be either saturated or unsaturated, but in general, saturated nitriles are preferably used. Specific examples include acetonitrile, propionitrile, succinonitrile, butyronitrile, isobutyronitrile, and the like.

The ethers are not particularly limited, which may be either cyclic or noncyclic, and may be either saturated or unsaturated, but in general, saturated ethers are preferably used. Specific examples include diethyl ether, methyl tert-butyl ether, anisole, dioxane, tetrahydrofuran, and the like.

In the method for production of the present invention, in light of toxicity to the human body and a wide range of applications and development for medical drugs, foods etc., alcohols are preferably used as the hydrophilic organic solvent, which may be more preferably alcohols having 1 to 5 carbon atoms, and most preferably ethanol.

Furthermore, when the hydrophilic organic solvent is used in the step (3), the concentration of the hydrophilic organic solvent contained in the aqueous phase is preferably 1 to 70% by volume, and more preferably 10 to 50% by volume. When the concentration of the hydrophilic organic solvent in the aqueous phase in method for production of the present invention exceeds 70% by volume, it may be difficult to obtain a stable S/O/W emulsion since the hydrophilic organic solvent is incorporated into the S/O suspension.

In the step (3), the surfactant (B), the thickening agent, or the hydrophilic organic solvent added into the aqueous phase may be used as a mixture of these, of course, and only one of these may be used alone.

In the step (3), the feeding proportion of the oil phase to the aqueous phase, i.e., the feeding proportion of the S/O suspension with respect to the aqueous phase containing at least one selected from the surfactant (B), the thickening agent and the hydrophilic organic solvents is not particularly limited, but the volume ratio of oil phase/aqueous phase is preferably 0.01/99.99 to 70/30, and more preferably 1/99 to 50/50.

In the step (3) of the method for production of the present invention, the means for adding the S/O suspension prepared in the step (2) into the aqueous phase and permitting liquid droplet dispersion to form an S/O/W emulsion is not particularly limited as long as it enables formation of the liquid droplet dispersion appropriately, and for example, stirring, a line mixer, porous plate dispersion, jet flowing, a pump or the like provides shearing, thereby permitting liquid droplet dispersion to prepare an S/O/W emulsion.

When the S/O/W emulsion is prepared by stirring, executed under a condition of a stirring power requirement per unit volume being 0.01 kW/m$^3$ or above is preferred, and the stirring power requirement is more preferably 0.1 kW/m$^3$ or above. Although the upper limit of the stirring power requirement is not particularly limited, too great stirring power requirement may result in, for example, vigorous entrainment of the bubble from the free surface of the liquid, leading to contamination of the bubble in the S/O/W emulsion. Accordingly obtaining a stable S/O/W emulsion may be difficult. Therefore, the upper limit of the stirring power requirement is preferably 1.5 kW/m$^3$ or below, and more preferably 1.0 kW/m$^3$ or below.

In the next step (4) of the method for production of the present invention, the S/O/W emulsion obtained in the step (3) is cooled to a temperature lower than the melting point of the solid fat to harden while maintaining the shape of the oil phase in the form of liquid droplets in the aqueous phase, and thereafter the moisture is removed at a temperature lower than the melting point of the solid fat to prepare S/O type microcapsules in which a hydrophilic bioactive substance is polydispersed in a solid fat matrix.

Although the method for cooling the S/O/W emulsion in the step (4) is not particularly limited, for example, a method in which the temperature in the apparatus used for preparing the S/O/W emulsion is gradually decreased to cool to a temperature of lower than the melting point of the solid fat, or a method in which rapid cooling is executed to harden the oil phase by charging the obtained S/O/W emulsion at once or gradually to an aqueous phase (noncoagulated aqueous phase) in an separate apparatus which had been adjusted beforehand to a temperature lower than the melting point of the solid fat, or by adding to the obtained S/O/W emulsion at once or gradually an aqueous phase which had been adjusted beforehand to a temperature lower than the melting point of the solid fat, and then mixing the S/O/W emulsion with the aqueous phase adjusted to a temperature lower than the melting point of the solid fat, or the like.

When the cooling rate is too high in the method of gradually cool the S/O/W emulsion in an apparatus, the homogeneity of the obtained S/O type microcapsules becomes too low, and controlling the particle size may be difficult due to generation of coarse particles and the like. Therefore, the cooling rate is preferably 0.5° C./min or below, and more preferably 0.2° C./min or below. Although the lower limit of the cooling rate is not particularly limited, enormously low cooling rate may cause problems of increase in frequency of pulverization during producing the S/O type microcapsules, and the like. Therefore, the cooling rate is preferably 0.01° C./min or above, and more preferably 0.05° C./min or above.

On the other hand, according to the method of rapid cooling executed by mixing the S/O/W emulsion with the aqueous phase having a temperature lower than the melting point of the solid fat, the solid fat being the oil phase instantly hardens; therefore, the S/O suspension dispersed in the aqueous phase changes into solid form particles while maintaining the dispersed state. This cooling method is a preferred method in terms of capability of achieving a high rate of encapsulation due to instant hardening of the oil phase, since leakage of the core substance can be suppressed as the contact chance of the hydrophilic bioactive substance being the core substance with the external aqueous phase is reduced. The aqueous phase to be mixed with the S/O/W emulsion in this method may be constituted with water alone, but in light of maintaining the dispersion state, and preventing association of oil droplets, the aqueous phase containing at least one selected from a surfactant (B), a thickening agent and a hydrophilic organic solvent as described above is preferred. In this instance, the surfactant (B), the thickening agent, the hydrophilic organic solvent and the like may be either the same as or different from those used in the step (3).

From the foregoing, a suspension liquid in which S/O type microcapsules are dispersed in an aqueous phase can be obtained. The S/O type microcapsules obtained in this manner are subjected to solid-liquid separation by, for example, decantation, centrifugal separation, compression filtration, reduced pressure filtration, natural filtration or the like while maintaining the temperature at lower than the melting point of the solid fat, and further subjected to cake washing as needed. Furthermore, a dry processing such as vacuum drying may be carried out to remove the moisture. Accordingly, the S/O type microcapsules can be obtained as dry particles.

The mean particle size of the S/O type microcapsules obtained by the method for production of the present invention may be adjusted appropriately based on the concentration of the surfactant fed in production, the stirring speed, the cooling rate, and the like. In the present invention, the mean particle diameter of the obtained S/O type microcapsules is preferably 1 to 2,000 μm, and when used for tablet applications and soft capsule applications, the mean particle size is preferably 50 to 300 μm. When the mean particle size of the S/O type microcapsules exceeds 300 μm, problems of, for example, nonuniform amount of tableting or filling in a soft capsule and the like may occur.

According to the method for production of the present invention, S/O type microcapsules in which a hydrophilic bioactive substance is polydispersed homogenously without deviation in the particle can be obtained. The "polydispersion" herein referred to means polynuclear dispersion of the hydrophilic bioactive substance in the microcapsules. Additionally, in light of the yield of the microcapsules in production and bioactive effects, the dispersed-particle diameter of the hydrophilic bioactive substance in the microcapsules falls within the range of preferably 0.01 to 50 μm, more preferably 0.01 to 20 μm, and most preferably 0.01 to 10 μm by controlling the amount of addition of the surfactant (A), the shearing strength during the W/O dispersion, and the like in the step (1).

The S/O type microcapsules obtained by the method for production of the present invention can be orally administered in the form without modification, or can be tabletted or filled in soft a capsule. Alternatively, they may be mixed with other material, and processed for use.

Furthermore, another aspect of the present invention is directed to S/O type microcapsules in which a particular hydrophilic bioactive substance, for example, glutathione or an imidazole dipeptide is polydispersed in a solid fat matrix. The imidazole dipeptide which may be used in the present invention is not particularly limited as long as it is a dipeptide having an imidazole skeleton, and histidine or its derivative bound to other amino acid, which is a histidine-containing dipeptide (HCDP), generally referred to can be preferably used. Specific examples of the imidazole dipeptide include anserine (β-alanyl-1-methylhistidine), carnosine (β-alanyl-histidine), balenine (β-alanyl-3-methylhistidine), homoanserine (N-(4-aminobutyryl)-L-histidine), N-acetyl-L-carnosine, and derivatives such as salts thereof. The salt of the imidazole dipeptide may include salts with hydrochloric acid, lactic acid, acetic acid, sulfuric acid, citric acid, ascorbic acid, malic acid, succinic acid, adipic acid, gluconic acid, tartaric acid or the like. Of these, anserine, carnosine and balenine are preferably used. These imidazole dipeptides are included in livestock meat and the like such as fish meat, whale meat, chicken meat etc., and can be obtained by extracting the same using a method such as water extraction, hot water extraction, alcohol extraction, supercritical extraction or the like. Thus obtained extract may be used directly, or after subjecting to purification as needed. Also, a commercially available product can be used directly. Alternatively, yeast, fungus dried matter, and foods highly containing an imidazole dipeptide can be also used.

Although the method for production of the glutathione-containing S/O type microcapsules, or the imidazole dipeptide-containing S/O type microcapsules of the present invention is not particularly limited, these may be preferably obtained by the aforementioned method for production of the present invention. By adopting the method for production of the present invention, S/O type microcapsules containing glutathione or an imidazole dipeptide at a high concentration can be obtained. The content of the active ingredient (glutathione or imidazole dipeptide) in the glutathione or imidazole dipeptide-containing S/O type microcapsules of the present invention is preferably 0.01 to 70% by weight, and more preferably 1 to 40% by weight relative to the total weight of the microcapsules.

Moreover, in the present invention, by using a component degradable with lipase, such as fats and oils, as the solid fat employed, enteric S/O type microcapsules can be also prepared. More specifically, one preferable aspect of the S/O type microcapsule of the present invention is a formulation that enables glutathione, an imidazole dipeptide or the like, which is a hydrophilic bioactive substance being likely to be degraded in stomach, to be absorbed efficiently in intestine without degradation in stomach.

Furthermore, when bulk powders accompanied by unpleasant odor components or unpleasant gustatory components which are derived from fishes, such as anserine bulk powders are utilized as the imidazole dipeptide, the active ingredient can be formulated to be enclosed in a solid fat by producing the S/O type microcapsules of the present invention. Therefore, masking effects of odors and tastes can be imparted.

Besides, when the S/O type microcapsules of an imidazole dipeptide are produced, commercially available dry imidazole dipeptide bulk powders may be used after dissolving in water beforehand, or an imidazole dipeptide concentrate extracted from fishes or the like may be directly used, which may be followed by dehydration and capsulation by a solid fat, thereby capable of producing S/O type microcapsules industrially efficiently.

EXAMPLES

Next, the present invention is specifically explained by way of Examples, but the present invention is not limited only to these Examples.

In the following Examples and Comparative Examples, the mean particle size of the microcapsules, the content of the hydrophilic bioactive substance in the microcapsules, and the encapsulation yield of the hydrophilic bioactive substance in the microcapsules were determined according to the following procedures.

Mean Particle Size of Microcapsules

A particle size analyzer (manufactured by Horiba, Ltd. LA-950) was used for determining the mean particle size.

Content of Hydrophilic Bioactive Substance in Microcapsules

The obtained microcapsules were heated to a temperature of at least the melting point of the solid fat employed to make them liquidified, and mixed with water. The hydrophilic bioactive substance encapsulated in the microcapsules was thereby extracted into an aqueous phase. The concentration of the extracted hydrophilic bioactive substance in the aqueous phase was determined with HPLC and the net content of the hydrophilic bioactive substance in the microcapsules was calculated.

Encapsulation Yield of Hydrophilic Bioactive Substance into Microcapsules

The encapsulation yield was calculated from the weight of the hydrophilic bioactive substance fed in the step (1), and the content of the hydrophilic bioactive substance in the microcapsules determined by the aforementioned method.

Example 1

Figure 1:
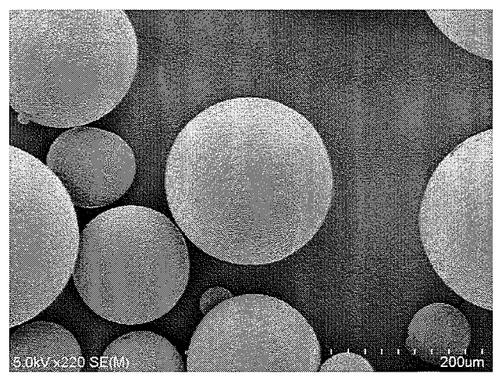
FIG. 1 shows an SEM photograph of S/P type microcapsules enclosing glutathione obtained in Example 1.

To an oily component consisting of 18 g of hydrogenated palm oil (melting point: 58° C.) and 0.9 g of tetraglycerol condensed ricinoleate (manufactured by Riken Vitamin Co., Ltd., POEM PR-100, HLB: 0.3) which had been heated to a temperature of 60° C. and melted beforehand was added 5 mL of an aqueous solution containing 20% by weight of glutathione (manufactured by Kaneka Corporation), followed by carrying out emulsification and dispersion at 63° C. with a homogenizer to prepare a W/O emulsion. Subsequently, the W/O emulsion was stirred for 30 min at a temperature of 70° C. under a vacuum condition with a pressure of 13 kPa to remove the moisture, whereby an S/O suspension was prepared. Thus resulting S/O suspension was added to 600 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 60° C. beforehand. The mixture was stirred at a temperature of 63° C. using a disk turbine blade with a stirring power requirement of 0.34 kW/m$^3$ to permit liquid droplet dispersion of the S/O suspension in the aqueous solution, whereby an S/O/W emulsion was prepared. Thereafter, the S/O/W emulsion was cooled to 40° C. while stirring at a cooling rate of 0.4° C./min to harden the oil phase, followed by vacuum filtration at room temperature (25° C.), and vacuum drying at 45° C. to obtain S/O type microcapsules. The mean particle size of the resulting microcapsules was 132 µm, and the content of glutathione in the microcapsules was 4.5% by weight. In addition, the encapsulation yield of glutathione in the microcapsules according to this Example was 89.1%. Moreover, when the obtained S/O type microcapsules were observed with a scanning electron microscope (manufactured by Hitachi, Ltd., S-800), particle shapes having a smooth surface structure were found as shown in FIG. 1.

Example 2

To an oily component consisting of 18 g of hydrogenated palm oil (melting point: 58° C.) and 0.9 g of tetraglycerol condensed ricinoleate (manufactured by Riken Vitamin Co., Ltd., POEM PR-100, HLB: 0.3) which had been heated to a temperature of 60° C. and melted beforehand was added 5 mL of an aqueous solution containing 30% by weight of glutathione (manufactured by Kaneka Corporation), followed by carrying out emulsification and dispersion at 63° C. with a homogenizer to prepare a W/O emulsion. Subsequently, the W/O emulsion was stirred for 30 min at a temperature of 70° C. under a vacuum condition with a pressure of 13 kPa to remove the moisture, whereby an S/O suspension was prepared. Thus resulting S/O suspension was added to 300 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 60° C. beforehand. The mixture was stirred at a temperature of 63° C. using a disk turbine blade with a stirring power requirement of 0.34 kW/m$^3$ to permit liquid droplet dispersion of the S/O suspension in the aqueous solution, whereby an S/O/W emulsion was prepared. Thereafter, the S/O/W emulsion was rapidly cooled by charging at once into 300 mL of an aqueous solution containing gum arabic (0.5% by weight) and decaglycerol monooleate (0.05% by weight) which had been cooled to 15° C. beforehand to harden the oil phase, followed by vacuum filtration at room temperature (25° C.), and vacuum drying at 45° C. to obtain S/O type microcapsules. The mean particle size of the resulting microcapsules was 140 µm, and the content of glutathione in the microcapsules was 6.3% by weight. In addition, the encapsulation yield of glutathione in the microcapsules according to this Example was 85.6%.

Example 3

To an oily component consisting of 18 g of a fractionated palm fat (melting point: 42° C.) and 0.9 g of tetraglycerol condensed ricinoleate (manufactured by Riken Vitamin Co., Ltd., POEM PR-100, HLB: 0.3) which had been heated to a temperature of 50° C. and melted beforehand was added 5 mL of an aqueous solution containing 30% by weight of glutathione (manufactured by Kaneka Corporation), followed by carrying out emulsification and dispersion at 47° C. with a homogenizer to prepare a W/O emulsion. Subsequently, the W/O emulsion was stirred for 30 min at a temperature of 70° C. under a vacuum condition with a pressure of 13 kPa to remove the moisture, whereby an S/O suspension was prepared. Thus resulting S/O suspension was added to 300 mL of an aqueous solution containing gum arabic (0.5% by weight), decaglycerol monooleate (manufactured by Riken Vitamin Co., Ltd., POEM J-0381V, HLB: 12) (0.05% by weight) and ethanol (30% by volume) which had been heated to 50° C. beforehand. The mixture was stirred at a temperature of 47° C. using a disk turbine blade with a stirring power requirement of 0.34 kW/m$^3$ to permit liquid droplet dispersion of the S/O suspension in the aqueous solution, whereby an S/O/W emulsion was prepared. Thereafter, the S/O/W emulsion was rapidly cooled by charging at once into 300 mL of an aqueous solution containing gum arabic (0.5% by weight), decaglycerol monooleate (0.05% by weight) and ethanol (30% by volume) which had been cooled to 15° C. beforehand to harden the oil phase, followed by vacuum filtration at room temperature (25° C.), and vacuum drying at the same temperature to obtain S/O type microcapsules. The mean particle size of the resulting microcapsules was 195 μm, and the content of glutathione in the microcapsules was 6.5% by weight. In addition, the encapsulation yield of glutathione in the microcapsules according to this Example was 88.6%.

Example 4

To an oily component consisting of 20 g of hydrogenated palm oil (melting point: 58° C.) and 1.0 g of tetraglycerol condensed ricinoleate (manufactured by Riken Vitamin Co., Ltd., POEM PR-100, HLB: 0.3) which had been heated to a temperature of 60° C. and melted beforehand was added 10 mL of an aqueous solution containing 30% by weight of glutathione (manufactured by Kaneka Corporation), followed by carrying out emulsification and dispersion at 63° C. with a homogenizer to prepare a W/O emulsion. Subsequently, the W/O emulsion was stirred for 30 min at a temperature of 70° C. under a vacuum condition with a pressure of 13 kPa to remove the moisture, whereby an S/O suspension was prepared. An operation of adding 10 mL of a 30% by weight glutathione (manufactured by Kaneka Corporation) aqueous solution to the S/O suspension again to prepare a W/O emulsion similarly, and removing the moisture to prepare an S/O suspension was repeated three times in total to obtain an S/O suspension in which glutathione is dispersed at a high content. Thus resulting S/O suspension was added to 300 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 60° C. beforehand. The mixture was stirred at a temperature of 63° C. using a disk turbine blade with a stirring power requirement of 0.34 kW/m$^3$ to permit liquid droplet dispersion of the S/O suspension in the aqueous solution, whereby an S/O/W emulsion was prepared. Thereafter, the S/O/W emulsion was rapidly cooled by charging at once into 300 mL of an aqueous solution containing gum arabic (0.5% by weight) and decaglycerol monooleate (0.05% by weight) which had been cooled to 15° C. beforehand to harden the oil phase, followed by vacuum filtration at room temperature (25° C.), and vacuum drying at 45° C. to obtain S/O type microcapsules. The mean particle size of the resulting microcapsules was 220 μm, and the content of glutathione in the microcapsules was 25.1% by weight. In addition, the encapsulation yield of glutathione in the microcapsules according to this Example was 83.7%.

Example 5

To an oily component consisting of 40 g of hardened rape seed oil (melting point: 65° C.) and 2.0 g of tetraglycerol condensed ricinoleate (manufactured by Riken Vitamin Co., Ltd., POEM PR-100, HLB: 0.3) which had been heated to a temperature of 70° C. and melted beforehand was added 40 mL of an aqueous solution containing 4% by weight of anserine (manufactured by Yaizu Suisankagaku Industry Co., Ltd.), followed by carrying out emulsification and dispersion at 70° C. with a homogenizer to prepare a W/O emulsion. Subsequently, the W/O emulsion was stirred for 30 min at a temperature of 75° C. under a vacuum condition with a pressure of 13 kPa to remove the moisture, whereby an S/O suspension was prepared. Thus resulting S/O suspension was added to 300 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 70° C. beforehand. The mixture was stirred at a temperature of 70° C. using a disk turbine blade with a stirring power requirement of 0.34 kW/m$^3$ to prepare an S/O/W emulsion. Thereafter, the S/O/W emulsion was rapidly cooled by charging at once into 300 mL of an aqueous solution containing gum arabic (0.5% by weight) and decaglycerol monooleate (0.05% by weight) which had been cooled to 15° C. beforehand to harden the oil phase, followed by vacuum filtration at room temperature (25° C.), and vacuum drying at 45° C. to obtain S/O type microcapsules. The mean particle size of the resulting microcapsules was 285 μm, and the content of anserine in the microcapsules was 3.1% by weight. In addition, the encapsulation yield of the anserine in the microcapsules according to this Example was 89.0%.

Example 6

S/O type microcapsules were obtained with a similar method and conditions to those in Example 2 except that an aqueous solution containing 20% by weight of ascorbic acid (manufactured by Wako Pure Chemical Industries, Ltd.) was used in place of the glutathione-containing aqueous solution. The mean particle size of the resulting microcapsules was 153 μm, and the content of ascorbic acid in the microcapsules was 4.4% by weight. In addition, the encapsulation yield of the ascorbic acid in the microcapsules according to this Example was 87.0%.

Comparative Example 1

To an oily component consisting of 18 g of hydrogenated palm oil (melting point: 58° C.) and 0.9 g of tetraglycerol condensed ricinoleate (manufactured by Riken Vitamin Co., Ltd., POEM PR-100, HLB: 0.3) which had been heated to a temperature of 60° C. and melted beforehand was added 1.0 g of glutathione (manufactured by Kaneka Corporation), followed by carrying out dispersion at 63° C. with a homogenizer to obtain a glutathione-containing composition. Thus resulting glutathione-containing composition was added to 300 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 60° C. beforehand. The mixture was stirred at a temperature of 63° C. using a disk turbine blade with a stirring power requirement of 0.34 kW/m$^3$ to permit emulsification and mixing, and then was rapidly cooled by charging into 300 mL of an aqueous solution containing gum arabic (0.5% by weight) and decaglycerol monooleate (0.05% by weight) which had been cooled to 15° C., followed by vacuum filtration at room temperature (25° C.), and vacuum drying at 45° C. to obtain S/O type microcapsules. The mean particle size of the resulting microcapsules was 151 μm, and the content of glutathione in the microcapsules was 2.9% by weight. In addition, the encapsulation yield of glutathione in the microcapsules according to this Example was 58.3%.

Comparative Example 2

To an oily component consisting of 18 g of hydrogenated palm oil (melting point: 58° C.) and 0.9 g of tetraglycerol condensed ricinoleate (manufactured by Riken Vitamin Co., Ltd., POEM PR-100, HLB: 0.3) which had been heated to a temperature of 60° C. and melted beforehand was added 5 mL of an aqueous solution containing 20% by weight of glutathione (manufactured by Kaneka Corporation), followed by carrying out emulsification and dispersion at 63° C. with a homogenizer to prepare a W/O emulsion. Thus resulting W/O emulsion was added to 600 mL of an aqueous solution containing gum arabic (0.5% by weight) and decaglycerol monooleate (manufactured by Riken Vitamin Co., Ltd., POEM J-0381V, HLB: 12) (0.05% by weight) which had been heated to 60° C. beforehand. The mixture was stirred at a temperature of 63° C. using a disk turbine blade with a stirring power requirement of 0.34 kW/m³ to prepare a W/O/W emulsion. Thereafter, the W/O/W emulsion was cooled to 40° C. while keeping stirring at a cooling rate of 0.4° C./min to harden the oil phase, followed by vacuum filtration at room temperature (25° C.), and vacuum drying at 45° C. to obtain W/O type microcapsules. The mean particle size of the resulting microcapsules was 110 μm, and the content of glutathione in the microcapsules was 2.1% by weight. In addition, the encapsulation yield of glutathione in the microcapsules according to this Example was 41.7%.

Comparative Example 3

To an oily component consisting of 18 g of hydrogenated palm oil (melting point: 58° C.) and 0.9 g of tetraglycerol condensed ricinoleate (manufactured by Riken Vitamin Co., Ltd., POEM PR-100, HLB: 0.3) which had been heated to a temperature of 60° C. and melted beforehand was added 5 mL of an aqueous solution containing 20% by weight of glutathione (manufactured by Kaneka Corporation), followed by carrying out emulsification and dispersion at 63° C. with a homogenizer to prepare a W/O emulsion. Subsequently, the W/O emulsion was stirred for 30 min at a temperature of 70° C. under a vacuum condition with a pressure of 13 kPa to remove the moisture, whereby an S/O suspension was prepared. The resulting S/O suspension was added to 600 mL of water which had been heated to 60° C. beforehand, and the mixture was stirred at a temperature of 63° C. using a disk turbine blade with a stirring power requirement of 0.34 kW/m³ to permit liquid droplet dispersion of the S/O suspension in the aqueous solution, whereby an S/O/W emulsion was prepared. Thereafter, the S/O/W emulsion was cooled while keeping stirring at a cooling rate of 0.4° C./min; however, aggregation of dispersed droplets of the oily component occurred when the temperature was 48° C. to produce an aggregated oil-based composition, and thus obtaining S/O type microcapsules failed.

Table 1 shows experimental conditions in Examples 1 to 5, and Comparative Examples 1 to 2, as well as results of determination of the particle size, the core substance content and the encapsulation yield of the obtained S/O type microcapsules.

TABLE 1

| | Example 1 | Example 2 | Example 3 | Example 4 | Example 5 | Example 6 | Comparative Example 1 | Comparative Example 2 |
|---|---|---|---|---|---|---|---|---|
| Solid fat | hydrogenated palm oil, melting point: 58° C. | hydrogenated palm oil, melting point: 58° C. | fractionated palm fat, melting point: 42° C. | hydrogenated palm oil, melting point: 58° C. | hardened rape seed oil, melting point: 65° C. | hydrogenated palm oil, melting point: 58° C. | hydrogenated palm oil, melting point: 58° C. | hydrogenated palm oil, melting point: 58° C. |
| Core substance | glutathione | glutathione | glutathione | glutathione | anserine | ascorbic acid | glutathione | glutathione |
| Dehydration of W/O to S/O | done | done | done | done (three-times dehydration) | done | done | not done | done |
| Cooling procedure | −0.4° C./min | rapid cooling | rapid cooling | rapid cooling | rapid cooling | rapid cooling | rapid cooling | −0.4° C./min |
| Form of microcapsules | S/O | S/O | S/O | S/O | S/O | S/O | S/O | W/O |
| Particle size [μm] | 132 | 140 | 195 | 220 | 285 | 153 | 151 | 110 |
| Core substance content [wt/%] | 4.5 | 6.3 | 6.5 | 25.1 | 3.1 | 4.4 | 2.9 | 2.1 |
| Encapsulation yield [%] | 89.1 | 85.6 | 88.6 | 83.7 | 89.0 | 87.0 | 58.3 | 41.7 |

The invention claimed is:

1. A method for production of S/O type microcapsules in which a hydrophilic bioactive substance is polydispersed in a solid fat matrix, said method comprising the following steps (1) to (4) of:
   (1) emulsifying and dispersing a mixture of the solid fat and an aqueous solution containing the hydrophilic bioactive substance at a temperature of at least the melting point of the solid fat to obtain a W/O emulsion;
   (2) removing moisture in the W/O emulsion at a temperature of at least the melting point and lower than the boiling point of the solid fat to obtain an S/O suspension;
   (3) adding the S/O suspension into an aqueous phase containing at least one selected from the group consisting of a surfactant (B), a thickening agent and a hydrophilic organic solvent, and permitting liquid droplet dispersion at a temperature of at least the melting point and lower than the boiling point of the solid fat to obtain an S/O/W emulsion; and
   (4) cooling the S/O/W emulsion to lower than the melting point of the solid fat to harden the solid fat, and further removing the moisture at a temperature lower than the melting point of the solid fat.

2. The method for production according to claim 1, wherein the solid fat has a melting point of at least 40° C.

3. The method for production according to claim 1, wherein the weight ratio of the hydrophilic bioactive substance to the solid fat in the step (1) falls within the range of 0.01/99.99 to 70/30.

4. The method for production according to claim 1, wherein a surfactant (A) is contained in the oil phase of the W/O emulsion in the step (1).

5. The method for production according to claim 4, wherein the surfactant (A) exhibits an HLB of 10 or below, and is at least one selected from the group consisting of sucrose esters of fatty acids, glycerol esters of fatty acids, sorbitan esters of fatty acids, and lecithins.

6. The method for production according to claim 4, wherein the content of the surfactant (A) in the oil phase is at least 0.01% by weight.

7. The method for production according to claim 1, wherein the surfactant (B) which exhibits an HLB of 5 or above, and which is selected from the group consisting of sucrose esters of fatty acids, glycerol esters of fatty acids, sorbitan esters of fatty acids, and lecithins is used in the step (3).

8. The method for production according to claim 7, wherein the content of the surfactant (B) in the aqueous phase is at least 0.001% by weight.

9. The method for production according to claim 1, wherein at least one thickening agent selected from the group consisting of gum arabic, gelatin, agar, starch, carrageenan, casein, alginic acids, saccharides, pullulan, celluloses, xanthan gum, guar gum, tamarind seed gum, and polyvinyl alcohols is used in the step (3).

10. The method for production according to claim 9, wherein the content of the thickening agent in the aqueous phase is 0.001 to 10% by weight.

11. The method for production according to claim 1, wherein at least one hydrophilic organic solvent selected from the group consisting of ketones, alcohols, nitriles, and ethers is used in the step (3).

12. The method for production according to claim 11, wherein the content of the hydrophilic organic solvent in the aqueous phase is 1 to 70% by volume.

13. The method for production according to claim 1, wherein the means for permitting the liquid droplet dispersion of the S/O suspension in the aqueous phase in the step (3) is at least one selected from the group consisting of shearing processes by stirring, a line mixer, porous plate dispersion, jet flowing, and a pump.

14. The method for production according to claim 13, wherein the shearing process in the step (3) is stirring carried out under conditions of a stifling power requirement per unit volume being 0.01 kW/m$^3$ or above.

15. The method for production according to claim 1, wherein the cooling rate in the cooling in the step (4) falls within the range of 0.01 to 0.5° C./min.

16. The method for production according to claim 1, wherein the cooling in the step (4) is rapid cooling executed by mixing the S/O/W emulsion with an aqueous phase having a temperature lower than the melting point of the solid fat.

* * * * *